United States Patent [19]
Glastra

[11] Patent Number: 5,653,736
[45] Date of Patent: Aug. 5, 1997

[54] CARRIER BALLOON FOR A STENT ASSEMBLY WITH RADIATION-SHIELDING CAPABILITIES

[75] Inventor: Hendrik Glastra, Enschede, Netherlands

[73] Assignee: Cordis Corporation, Miami Lakes, Fla.

[21] Appl. No.: 588,455

[22] Filed: Jan. 18, 1996

[30] Foreign Application Priority Data

Jan. 19, 1995 [NL] Netherlands ............................ 9500095

[51] Int. Cl.$^6$ ........................................................ A61B 17/34
[52] U.S. Cl. .......................... 606/198; 606/194; 606/191
[58] Field of Search .................................... 606/195, 194, 606/198, 192, 191; 623/1, 12; 604/96, 104

[56] References Cited

U.S. PATENT DOCUMENTS 5,100,429  3/1992  Sinofsky et al. ...................... 606/195
5,443,495  8/1995  Buscemi et al. ...................... 623/1

Primary Examiner—Michael Buiz
Assistant Examiner—Kevin Truong
Attorney, Agent, or Firm—Lockwood, Alex, Fitzgibbon & Cummings

[57] ABSTRACT

An improved carrier balloon for a stent assembly with radiation-shielding capabilities includes an inflatable, comprising an expandable sleeve enclosing the balloon and an expandable stent in the form of a sleeve filled with a material which sets under the influence of radiation. A radiation conducting optical fiber extend within the balloon and confronts a material impervious to radiation disposed within the balloon at its front end. This material prevents the radiation used for curing the stent from reaching the blood and/or body tissue of a patient.

20 Claims, 1 Drawing Sheet

CARRIER BALLOON FOR A STENT ASSEMBLY WITH RADIATION-SHIELDING CAPABILITIES

BACKGROUND AND SUMMARY OF THE INVENTION

The present invention relates generally to balloon assemblies used for intraluminally delivering stents and, more particularly to an expandable carrier balloon for a stent assembly which sets under the influence of radiation.

Stents are widely used to repair or reinforce weakened blood vessels. Stents may be inserted into blood vessels in a number of ways. They may be implanted by surgery, wherein a diseased or otherwise compromised portion of the blood vessel is removed and the stent inserted in its place or they may be intraluminally delivered. That is, the stents may be mounted on a catheter and introduced through the blood vessel to the compromised section and left in place. In this latter means of stent placement, the catheter used typically has an expandable balloon section and the stent is carried upon the balloon into the blood vessel and the balloon is expanded which causes the stent also to expand into place within the blood vessel.

Certain stents which are inserted by such balloons are made from radiation-curable materials so that after the stent has been expanded into place in the blood vessel, the stent is subjected to radiation for a specific amount of time to cure the stent material so that it sets in place.

Radiation-cured expandable stents and insertion catheters therefor are disclosed in my prior European Patent Applications EP-A-0 521 573 and EP-A-0 617 930.

When using these known stent assemblies, a balloon is rolled up and connected to the distal end of the delivery catheter. A stent is also rolled up and connected to the distal end of the catheter over the balloon to form a balloon-stent assembly. This assembly is positioned at the desired location within a body vessel by manipulation of the catheter. The stent is expanded in place by inflating the balloon under pressure from an inflation media pumped through the catheter. Such a stent is made of a radiation-curable or radiation-setting material which hardens under the influence of radiation (typically either ultraviolet or laser radiation) supplied through a fiber-optic cable extending through the catheter.

The radiation exits the end of the fiber-optic cable as described in European Patent Application EP-A-0 617 930 and is for the major part absorbed by the setting material of the stent in such a way that most of the radiation doers not reach the tissue or blood of the catheterized patient. However, it has been found in some instances that the radiation may exit the front end of the balloon catheter and reach the tissue or blood of the patient. This radiation may prove to be detrimental to blood or to body tissues in some instances.

The present invention is therefore directed to a balloon catheter with radiation-shielding properties to eliminate radiation "leakage" from the catheter during expansion and setting of the stent.

In a preferred embodiment of the invention, a balloon catheter is provided with one or more internal optical fibers which convey light-wave radiation, such as laser or ultraviolet radiation to the balloon portion of the catheter. The front, or distal end, of the balloon is provided with a radiation shield such that the dissemination of radiation is controlled to thereby prevent the exposing the tissue or blood of the patient to unwanted radiation.

The radiation-shielding material is preferably disposed within the balloon and is radiation reflecting so that it reflects the radiation back into the body of balloon where it may impinge upon the radiation-curable material forming the stent.

Accordingly, it is a general object of the present invention to provide a carrier assembly for an insertable stent, the stent being expandable and curable under the influence of radiation and the carrier assembly having an improved radiation delivery system.

Another object of the present invention is to provide a stent carrier assembly for intraluminally delivering a stent to a predesired location within a blood vessel, the stent carrier assembly including a catheter, an inflatable balloon disposed on the distal end of the catheter which may be selectively inflated and deflated, an expandable stent disposed on the catheter around the balloon, the stent being at least partially formed from a radiation-curable material, at least one optic fiber extending through the catheter into the balloon into position therewithin to disperse radiation to the stent after expansion and a radiation shield disposed within the balloon opposite the free end of the optic fiber to reduce the amount of unwanted radiation transmitted into the surrounding body tissue and/or blood.

It is a still further object of the present invention to provide an expandable carrier balloon assembly for the intraluminal delivery of an expandable stent in the form of a catheter having an inflatable balloon portion, an expandable stent disposed on the inflatable balloon, the stent being formed from a radiation-curable material, the balloon catheter having at least one radiation-transmitting member extending the length of the catheter and terminating within the balloon and the balloon having a radiation-reflecting portion which directs the radiation from the optic fiber back to the stent and prevents extraneous transmission of radiation outside of the balloon.

These and other objects, features and advantages of the present invention will be clearly understood through a consideration of the following detailed description.

BRIEF DESCRIPTION OF THE DRAWINGS

In the course of the following detailed description, reference will be frequently made to the accompanying drawings in which.

DETAILED DESCRIPTION OF THE PREFERRED EMBODIMENT

Figure 1:
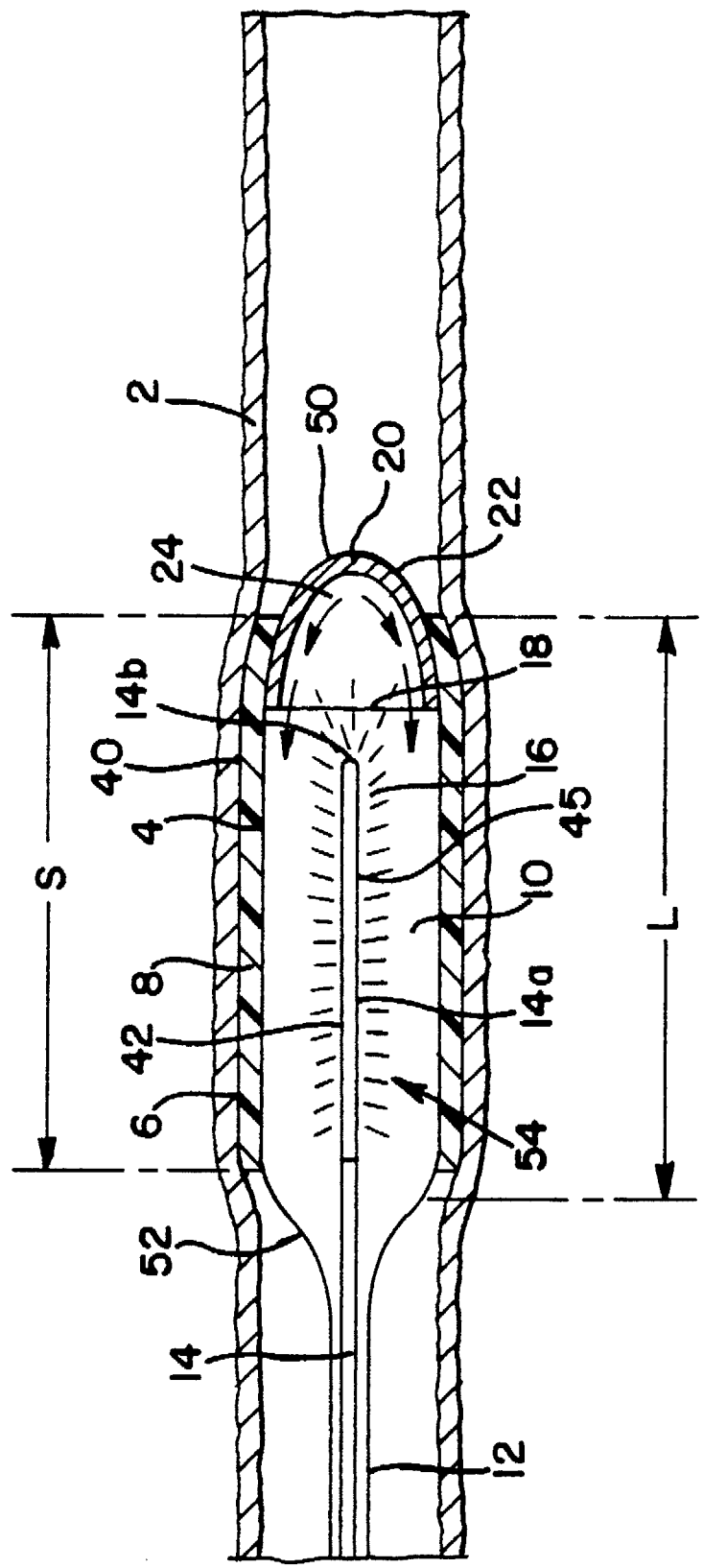
FIG. 1 is a longitudinal sectional view of a blood vessel with a stent carrier assembly constructed in accordance of the principles of the present invention shown in place within the blood vessel.

In FIG. 1, a blood vessel 2 is illustrated which is typical of the type in which the elongated stent 4 is arranged. This stent is of the kind as described in applicant's prior European patent applications EP-A-0 521 593 and EP-A-0 617 930. As described in those publications, the stent 4 comprises a double-walled sleeve 6 having an annular space 40 therebetween. This space 40 is filled with a setting or curable material 8 which is activated by light-wave radiation. By "setting" or "curable", a material is meant which sets or hardens when exposed to radiation of a particular wave length. Acrylates are an example of known curable materials suitable for use in forming the stent 4.

The stent 4 is arranged in the correct position intraluminally within the blood vessel 2 by means of an elongated catheter 12 which is inserted into the blood vessel 2 and traversed therethrough until it is positioned in the area of a compromised section of the blood vessel 2. The stent 4 is expanded by means of an expandable balloon 10 which is arranged at the distal end of the catheter 12. The balloon 10 has a working length L which is approximately equal to the length of the balloon outer surface which impacts against the walls of the blood vessel 2 when inflated. Typically, this length is no greater than the length S of the stent 4. When the balloon is inflated in place, it can be seen that two opposing forward and rearward ends 50, 52 are respectively defined in the balloon 10 in place within the expanded stent 4.

In order to set the stent in place within the blood vessel after expansion, the catheter 12 preferably has a fiber-optic cable or fiber 14 which extends for substantially the entire length of the catheter 12 and well into the interior of the balloon 10 as illustrated. The distal end 14a of the optical fiber 14 extends up into the balloon 10 while the proximal end 14b of the fiber 14 cooperates with a source of radiation e.g. a source of ultraviolet radiation or a laser, (not shown). The radiation is transmitted for the length of the catheter 12 along the optic fiber 14 and is emitted at the distal end 14a of the fiber 14 along a radiation-emitting portion 54 of the optic fiber 14. The radiation so emitted starts and accelerates the setting process of the curable material 8 from which the stent 4 is formed.

As illustrated in FIG. 1, the radiation is emitted along the surface 42 of the optic fiber 14 at the radiation-emitting portion 54 by means known in the art, such as notches, openings or other types of surface interruptions 45 formed in the surface of the fiber 14. Despite these radiation emission openings 45 on the fiber 14, radiation is also emitted from the forward end portion 14b of the fiber 14, i.e., along the longitudinal axis of the fiber 14.

The radiation emitted from the fiber 14 (illustrated as rays 16 in FIG. 1) along its outer surface 42 is absorbed by the curable material 8 in the stent 4 and therefore cannot endanger the patient. However, in order to substantially reduce and prevent the radiation 18 leaving the front end 14b of the optical fiber from contacting tissue or blood of the patient, the present invention provides a radiation-impervious shielding 22 applied to the front end 20 of the balloon 10. This shielding 22 may be provided as an integrated layer of balloon material or it may be applied as a separate coating either to the interior or exterior surfaces of the balloon 10, with FIG. 1 illustrating the shielding 22 being disposed along the interior surface of the balloon 10. As illustrated, the shielding 22 occupies the entirety of the balloon front end 50 and even preferably extends rearwardly along the working length L of the balloon 10 until it just passes the forward end of the stent 4. This shielding 22 adopts the configuration of the balloon forward end 50, which is generally hemispherical.

The shielding 22 may be radiation-reflective, so that radiation impinging thereon, indicated by arrows with 24, is reflected back into the balloon and thereby along the curable material 8 of the stent 4. However, it will be understood that a radiation absorbing coating would give comparable results in blocking the radiation but not reflecting it rearward.

While the preferred embodiment of the invention have been shown and described, it will be understood by those skilled in the art the changes or modifications may be made thereto without departing from the true spirit and scope of the invention.

I claim:

1. A stent carrier assembly for inserting a stent into a blood vessel comprising: a dilation catheter having an inflatable balloon affixed to a distal end thereof, a stent disposed on said inflatable balloon, the stent including an expandable sleeve formed from a radiation-curable material, a fiber-optic conduit disposed in said catheter and extending to said distal end thereof for conducting radiation to said stent for curing it in place after expansion, the distal end of said balloon having a radiation shielding disposed in association therewith to substantially prevent the transmission of radiation out of said balloon along a longitudinal axis of said assembly, said radiation shielding being generally hemispherical in configuration.

2. The stent carrier assembly as claimed in claim 1, wherein said radiation shielding is formed from a radiation-reflecting material.

3. The stent carrier assembly as claims in claim 1, wherein said radiation shielding is formed from a radiation-absorbing material.

4. The stent carrier assembly as claimed in claim 1, wherein said radiation shielding is in the form of a coating disposed on an interior surface of said balloon.

5. The stent carrier assembly as claimed in claim 1, wherein said radiation shielding forms a concave radiation barrier which reflects radiation emitted from said fiber optic conduit rearwardly along the interior of said balloon.

6. The stent carrier assembly as claimed in claim 1, wherein said fiber optic conduit has a radiation-emitting portion which extends for at least one-half of the length of said expandable stent.

7. The stent carrier assembly as claimed in claim 1, wherein said radiation-curable material is an acrylate.

8. The stent carrier assembly as claimed in claim 1, wherein said balloon is substantially transparent.

9. The stent carrier assembly as claimed in claim 1, wherein said balloon has a front end portion projecting past an end of said sleeve and said radiation shielding said balloon projecting portion.

10. A catheter assembly for inserting a stent into a blood vessel by expanding the stent against the walls of the blood vessel and subjecting the stent to radiation to cure it so that it adopts its expanded position within said blood vessel, the catheter assembly comprising:

an elongated catheter with a dilation balloon disposed on the catheter at its distal end, the balloon having a given working length at which the balloon expands against said blood vessel walls under pressure from an inflation media, a stent in the form of an expandable sleeve having a length no greater than said balloon working length so that when said balloon is expanded, opposing forward and rearward ends of said balloon generally project out from opposing ends of said sleeve, said sleeve having a layer of radiation-curable material which hardens when exposed to radiation, a fiber-optic cable extending through said catheter into said balloon for conveying light radiation to said catheter distal end, the fiber-optic cable having an emission end which emits light through portions of its outer surface and its distal end, the emission end having a length no greater than said balloon working length, and said balloon having a radiation shielding layer incorporated therein substantially providing a radiation shield for said forward end of said balloon which prevents radiation emitted from said fiber-optic cable from exiting said balloon into said blood vessel, said radiation shielding layer extending from said balloon forward edges to just rearward of said sleeve formed end.

11. The catheter assembly of claim 10, wherein said radiation-curable material is an acrylate.

12. The catheter assembly of claim 10, wherein said radiation shielding layer is disposed on an interior surface of said balloon.

13. The catheter assembly of claim 10, wherein said balloon is formed from a substantially transparent material.

14. The catheter assembly of claim 10, wherein said radiation shielding layer is formed from a radiation-reflective material.

15. The catheter assembly of claim 10, wherein said radiation shielding layer is in the form of a coating disposed on said balloon forward end.

16. An intraluminal delivery assembly for an expandable stent, comprising: a catheter, an inflatable balloon disposed at a distal end of the catheter, an expandable stent formed from a radiation-curable material disposed on said balloon, means for emitting radiation through said balloon to said radiation-curable material when said stent is expanded by inflation of said balloon, said radiation-emitting means including a fiber-optic cable extending within said balloon and within said stent, said assembly further including a radiation shield formed on said balloon at a forward face thereof, the radiation shield extending coterminous with that portion of said balloon which extends out forwardly from within said stent when said balloon is inflated, said radiation shield preventing radiation emitted from said fiber-optic cable from entering the area surrounding said stent.

17. The intraluminal stent delivery assembly as claimed in claim 16, wherein said radiation shield is located along an interior surface of said balloon.

18. The intraluminal stent delivery assembly as claimed in claim 16, wherein said radiation shield includes a layer of reflective material which reflects radiation rearwardly within said balloon and along said stent.

19. A stent carrier assembly for inserting a stent into a blood vessel comprising: a dilation catheter having an inflatable balloon affixed to a distal end thereof, a stent disposed on said inflatable balloon, the stent including an expandable sleeve formed from a radiation-curable material, a fiber-optic conduit disposed in said catheter and extending to said distal end thereof for conducting radiation to said stent for curing it in place after expansion, the distal end of said balloon having a radiation shielding disposed on an interior surface of said balloon to substantially prevent the transmission of radiation out of said balloon along a longitudinal axis of said assembly.

20. A stent carrier assembly for inserting a stent into a blood vessel comprising: a dilation catheter having an inflatable balloon affixed to a distal end thereof, a stent disposed on said inflatable balloon, the stent including an expandable sleeve formed from a radiation-curable material, a fiber-optic conduit disposed in said catheter and extending to said distal end thereof for conducting radiation to said stent for curing it in place after expansion, the distal end of said balloon having a radiation shielding disposed in association therewith and extending along a portion of said balloon to substantially prevent the transmission of radiation out of said balloon along a longitudinal axis of said stent carrier assembly.

* * * * *